(12) United States Patent
Jansen et al.

(10) Patent No.: US 7,482,428 B2
(45) Date of Patent: Jan. 27, 2009

(54) OPTIMIZED EXPRESSION OF HPV 31 L1 IN YEAST

(75) Inventors: Kathrin U. Jansen, Doylestown, PA (US); Loren D. Schultz, Harleysville, PA (US); Michael P. Neeper, Collegeville, PA (US); Henry Z. Markus, Wyncote, PA (US)

(73) Assignee: Merck & Co., Ltd., Rahway, NJ (US)

( * ) Notice: Subject to any disclaimer, the term of this patent is extended or adjusted under 35 U.S.C. 154(b) by 0 days.

(21) Appl. No.: 11/879,905

(22) Filed: Jul. 19, 2007

(65) Prior Publication Data
US 2008/0166371 A1 Jul. 10, 2008

Related U.S. Application Data

(62) Division of application No. 10/551,057, filed as application No. PCT/US2004/008677 on Mar. 19, 2004, now Pat. No. 7,276,243.

(60) Provisional application No. 60/457,172, filed on Mar. 24, 2003.

(51) Int. Cl.
*A61K 38/00* (2006.01)
(52) U.S. Cl. ...................... 530/300; 530/350; 536/23.72
(58) Field of Classification Search .................. 530/300, 530/350; 536/23.72
See application file for complete search history.

(56) References Cited

U.S. PATENT DOCUMENTS

| | | | |
|---|---|---|---|
| 5,821,087 A | 10/1998 | Lowe et al. | |
| 6,159,729 A | 12/2000 | Hofmann et al. | |
| 6,180,363 B1 | 1/2001 | Batard et al. | |
| 6,436,402 B1 * | 8/2002 | Zhao et al. | 424/189.1 |
| 6,991,795 B1 * | 1/2006 | Lowe et al. | 424/185.1 |

FOREIGN PATENT DOCUMENTS

| | | |
|---|---|---|
| WO | WO 98/34640 A2 | 8/1998 |
| WO | WO 99/02694 A1 | 1/1999 |
| WO | WO 00/09157 A1 | 2/2000 |
| WO | WO 01/14416 A2 | 3/2001 |
| WO | WO 02/08435 A1 | 1/2002 |
| WO | WO 03/077942 A2 | 9/2003 |

OTHER PUBLICATIONS

Bosch, et al., "The causal relation between human papillomavirus and cervical cancer", J. Clin. Pathol., vol. 55, pp. 244-265, 2002.
Brietburd, et al., "Immunization with Viruslike Particles from Cottontail Rabbitt Papillomavirus (CRPV) Can Protect against Experimental CRPV Infection", Journal of Virology, vol. 69, No. 6, pp. 3959-3969, Jun. 1995.
Goldsborough, et al., "Nucleotide Sequence of Human Papillomavirus Type 31: A Cervical Neoplasia-Associated Virus", Virology, vol. 171, pp. 306-311, 1989.
Guo, et al., "3'-end-forming signals of yeast mRNA", TIBS 21, pp. 477-481, Dec. 1996.
Guo, et al., "Signals Sufficient for 3'-End Formation of Yeast mRNA", Molecular and Cellular Biology, vol. 16, No. 6, pp. 2772-2776, Jun. 1996.
Heidmann, et al., "Flexibility and Interchangeability of Polyadenylation Signals in *Saccharomyces cerevisiae*", Molecular and Cellular Biology, vol. 14, No. 7, pp. 4633-4642, Jul. 1994.
Henikoff, et al., "Transcription Terminates in Yeast Distal to a Control Sequence", Cell, vol. 33, pp. 607-614, Jun. 1983.
Icenogle, J. et al., "Sequence Variation in the Capsid Protein Genes of Human Papillomavirus Type 16 and Type 31", Virology, vol. 214, pp. 664-669, 1995.
Kotula & Curtis, "Evaluation of Foreign Gene Codon Optimization in Yeast: Expression of a Mouse IG Kappa Chain", Bio/Technology, vol. 9, pp. 1386-1389, Dec. 1991.
Liu, W. et al., "Polynucleotide viral vaccines: codon optimisation and ubiquitin conjugation enhances prophylactic and therapeutic efficacy", Vaccine, vol. 20, pp. 862-869, 2002.
McMurray, et al., "Biology of human papillomaviruses", Int. J. Exp. Path., vol. 82, pp. 15-33, 2001.
Russo, et al., "*Saccharomyces cerevisiae* mRNA 3'End Forming Signals are also Involved in Transcription Termination", Yeast, vol. 11, pp. 447-453, 1995.
Schiffman, et al., "Epidemiologic Evidence Showing That Human Papillomavirus Infection Causes Most Cervical Intraepithelial Neoplasia", J. of National Cancer Inst., vol. 85, No. 12, pp. 958-964, Jun. 16, 1993.
Schiller, et al., "Developing HPV virus-like particle vaccines to prevent cervical cancer: a progress report", J. of Clin. Virol., vol. 19, pp. 67-74, 2000.
Schiller, et al., "Papillomavirus-Like Particles Basic and Applied Studies", Papillomavirus Reviews: Current Research on Papillomaviruses, Lacey, et. Leeds, UK: Leeds Medical Information, pp. 101-112, 1996.
Sharp, et al., "Synonymous Codon Usage in *Saccharomyces cerevisiae*", Yeast, vol. 7, pp. 657-578, 1991.
Suzich, et al., "Systemic immunization with papillomavirus L1 protein completely prevents the development of viral mucosal papillomas", Proc. Natl. Acad. Sci. USA, vol. 92, pp. 11553-11557, Dec. 1995.

(Continued)

*Primary Examiner*—Ali R. Salimi
(74) *Attorney, Agent, or Firm*—Alysia A. Finnegan; Sheldon O. Heber

(57) ABSTRACT

Synthetic DNA molecules encoding the HPV31 L1 protein are provided. Specifically, the present invention provides polynucleotides encoding HPV31 L1 protein, wherein said polynucleotides are free from internal transcription termination signals that are recognized by yeast. Also provided are synthetic polynucleotides encoding HPV31 L1 wherein the polynucleotides have been codon-optimized for high level expression in a yeast cell. The synthetic molecules may be used to produce HPV31 virus-like particles (VLPs), and to produce vaccines and pharmaceutical compositions comprising the HPV31 VLPs. The vaccines of the present invention provide effective immunoprophylaxis against papillomavirus infection through neutralizing antibody and cell-mediated immunity.

14 Claims, 11 Drawing Sheets

OTHER PUBLICATIONS

Thalenfeld, et al., "oliI Transcripts in Wild-Type and in a Cytoplasmic "Petite" Mutant of Yeast", J. of Biological Chem., vol. 258, No. 23, pp. 14065-14068, 1983.

Tobery, T. et al., "Effect of vaccine delivery system on the induction of HPV16L1-specific humoral and cell-mediated immune responses in immunized rhesus macaques", Vaccine, 2003, vol. 21, pp. 1539-1547.

Zaret, et al., "DNA Sequence Required for Efficient Transcription Termination in Yeast", Cell, vol. 28, pp. 563-573, 1982.

Zaret, et al., "Mutationally Altered 3'Ends of Yeast CYC1 and mRNA Affect Transcript Stability and Translational Efficiency", J. Mol. Biol., vol. 176, pp. 107-135, 1984.

Zhou, et al., "Papillomavirus Capsid Protein Expression Level Depends on the Match Between Codon Usage and tRNA Availability", Journal of Virology, vol. 73, No. 6, Jun. 1999, pp. 4972-49823.

* cited by examiner

HPV 31 L1 nucleotide sequence alignment.

```
31 L1 wt       (   1) ATGTCTCTGTGGCGGCCTAGCGAGGCTACTGTCTACTTACCACCTGTCCC
31 L1 partial  (   1) ..................................................
31 L1 total    (   1) ......T.....A.A..ATCT..A.....C........G.....A.....

31 L1 wt       (  51) AGTGTCTAAAGTTGTAAGCACGGATGAATATGTAACACGAACCAACATAT
31 L1 partial  (  51) ..................................................
31 L1 total    (  51) ...C.....G..C..CTCT..C..C.....C..C..CA..........C.

31 L1 wt       ( 101) ATTATCACGCAGGCAGTGCTAGGCTGCTTACAGTAGGCCATCCATATTAT
31 L1 partial  ( 101) ..................................................
31 L1 total    ( 101) .C..C.....T..TTC......AT..T.G..C..C..T..C.....C..C 31 L1 wt       ( 151) TCCATACCTAAATCTGACAATCCTAAAAAAATAGTTGTACCAAAGGTGTC
31 L1 partial  ( 151) ..................................................
31 L1 total    ( 151) ..T..C..A..G........C...A..G..G..C..C..C........C..

31 L1 wt       ( 201) AGGATTACAATATAGGGTATTTAGGGTTCGTTTACCAGATCCAAACAAAT
31 L1 partial  ( 201) ..................................................
31 L1 total    ( 201) T..T..G.....C..A..C..C..A..CA.A..G.....C........G.

31 L1 wt       ( 251) TTGGATTTCCTGATACATCTTTTTATAATCCTGAAACTCAACGCTTAGTT
31 L1 partial  ( 251) ..................................................
31 L1 total    ( 251) .C..T..C..A..C..C.....C..C..C..A.....C...A.A..G..C 31 L1 wt       ( 301) TGGGCCTGTGTTGGTTTAGAGGTAGGTCGCGGGCAGCCATTAGGTGTAGG
31 L1 partial  ( 301) ..................................................
31 L1 total    ( 301) .....T.....C.....G..A..C...A.A..T..A.....G.....C..

31 L1 wt       ( 351) TATTAGTGGTCATCCATTATTAAATAAATTTGATGACACTGAAAACTCTA
31 L1 partial  ( 351) ..................................................
31 L1 total    ( 351) ...CTC......C.....G..G..C..G..C..C.....C.........

31 L1 wt       ( 401) ATAGATATGCCGGTGGTCCTGGCACTGATAATAGGGAATGTATATCAATG
31 L1 partial  ( 401) ..................................................
31 L1 total    ( 401) .C.....C..T........A..T..C..C..C..A........C..T...
```

FIG.1A

```
31 L1 wt       ( 451) GATTATAAACAAACACAACTGTGTTTACTTGGTTGCAAACCACCTATTGG
31 L1 partial  ( 451) ..................................................
31 L1 total    ( 451) ..C..C..G.....C...T.......GT.G.....T..G.....A..C..

31 L1 wt       ( 501) AGAGCATTGGGGTAAAGGTAGTCCTTGTAGTAACAATGCTATTACCCCTG
31 L1 partial  ( 501) ..................................................
31 L1 total    ( 501) T..A..C........G...TC...A...TC......C.....C.....A.

31 L1 wt       ( 551) GTGATTGTCCTCCATTAGAATTAAAAAAATTCAGTTATACAAGATGGGGAT
31 L1 partial  ( 551) ..................................................
31 L1 total    ( 551) ....C.....A.....G.....G..G..C..T..C..C.....C..T..C 31 L1 wt       ( 601) ATGGTTGATACAGGCTTTGGAGCTATGGATTTTACTGCTTTACAAGACAC
31 L1 partial  ( 601) ..................................................
31 L1 total    ( 601) .....C..C..C..T..C..T........C..C..C.....G........

31 L1 wt       ( 651) TAAAAGTAATGTTCCTTTGGACATTTGTAATTCTATTTGTAAATATCCAG
31 L1 partial  ( 651) ..................................................
31 L1 total    ( 651) C..GTC...C..C..A........C.....C.....C.....G..C....

31 L1 wt       ( 701) ATTATCTTAAAATGGTTGCTGAGCCATATGGCGATACATTATTTTTTTAT
31 L1 partial  ( 701) ........................C.....C..C..G..C..C..C..C
31 L1 total    ( 701) .C..CT.G..G.....C.....A.....C.....C..C..G..C..C..C 31 L1 wt       ( 751) TTACGTAGGGAACAAATGTTTGTAAGGCATTTTTTTAATAGATCAGGCAC
31 L1 partial  ( 751) ..G.....A.....G.....C........C..C..C..C.....C.....
31 L1 total    ( 751) ..G.....A.....G.....C........C..C..C..C.....C.....

31 L1 wt       ( 801) GGTTGGTGAATCGGTCCCTACTGACTTATATATTAAAGGCTCCGGTTCAA
31 L1 partial  ( 801) C..A........T.....A..C...C.G..C..C..G..........C.
31 L1 total    ( 801) C..A........T.....A..C...C.G..C..C..G..........C.

31 L1 wt       ( 851) CAGCTACTTTAGCTAACAGTACATACTTTCCTACACCTAGCGGCTCCATG
31 L1 partial  ( 851) .C.....CC.G......TCC..C.....C..A..T..ATCT.........
31 L1 total    ( 851) .C.....CC.G......TCC..C.....C..A..T..ATCT.........

31 L1 wt       ( 901) GTTACTTCAGATGCACAAATTTTTAATAAACCATATTGGATGCAACGTGC
31 L1 partial  ( 901) ..C..C..C..C...T..G..C..C..C..G.....C........G.....
31 L1 total    ( 901) ..C..C..C..C...T..G..C..C..C..G.....C........G.....
```

FIG. 1B

```
31 L1 wt      ( 951)  TCAGGGACACAATAATGGTATTTGTTGGGGCAATCAGTTATTTGTTACTG
31 L1 partial ( 951)  A.....T.....C..C.....C........T..C...C.G..C..G....
31 L1 total   ( 951)  A.....T.....C..C.....C........T..C...C.G..C..G....

31 L1 wt      (1001)  TGGTAGATACCACACGTAGTACCAATATGTCTGTTTGTGCTGCAATTGCA
31 L1 partial (1001)  ....C........G...TC......C.......C...........C..T
31 L1 total   (1001)  ....C........G...TC......C.......C...........C..T 31 L1 wt      (1051)  AACAGTGATACTACATTTAAAAGTAGTAATTTTAAAGAGTATTTAAGACA
31 L1 partial (1051)  ...TC...C.....C..C..GTCCTC...C..C..G.....CC.G.....
31 L1 total   (1051)  ...TC...C.....C..C..GTCCTC...C..C..G.....CC.G.....

31 L1 wt      (1101)  TGGTGAGGAATTTGATTTACAATTTATATTTCAGTTATGCAAAATAACAT
31 L1 partial (1101)  ..........C...C.G.....C..C..C.....G.....G..C..CC
31 L1 total   (1101)  ..........C...C.G.....C..C..C.....G.....G..C..CC 31 L1 wt      (1151)  TATCTGCAGACATAATGACATATATTCACAGTATGAATCCTGCTATTTTG
31 L1 partial (1151)  .G.....T.....C.....C..C..C..........C.....C..CC..
31 L1 total   (1151)  .G.....T.....C.....C..C..C..........C.....C..CC..

31 L1 wt      (1201)  GAAGATTGGAATTTTGGATTGACCACACCTCCCTCAGGTTCTTTGGAGGA
31 L1 partial (1201)  ..G..C.....C..C..TC.......T..A..T..C..........
31 L1 total   (1201)  ..G..C.....C..C..TC.......T..A..T..C...........A..

31 L1 wt      (1251)  TACCTATAGGTTTGTAACCTCACAGGCCATTACATGTCAAAAAAGTGCCC
31 L1 partial (1251)  ..................................................
31 L1 total   (1251)  C.....C..A..C..C.....T..A..T..C..C........GTC...T.

31 L1 wt      (1301)  CCCAAAAGCCCAAGGAAGATCCATTTAAAGATTATGTATTTTGGGAGGTT
31 L1 partial (1301)  ..................................................
31 L1 total   (1301)  .A........A........C.....C..G..C..C..C..C.....A..C 31 L1 wt      (1351)  AATTTAAAAGAAAAGTTTTCTGCAGATTTAGATCAGTTTCCACTGGGTCG
31 L1 partial (1351)  ..................................................
31 L1 total   (1351)  ..C..G..G........C.....T..C..G..C..A..C...T.....A.

31 L1 wt      (1401)  CAAATTTTTTATTACAGGCAGGATATAGGGCACGTCCTAAATTTAAAGCAG
31 L1 partial (1401)  ..................................................
31 L1 total   (1401)  A..G..C..G..G..A..T..T..C..A..TA.A..A..G..C..G..T.
```

FIG.1C

```
31 L1 wt      (1451)  GTAAACGTAGTGCACCCTCAGCATCTACCACTACACCAGCAAAACGTAAA
31 L1 partial (1451)  ..................................................
31 L1 total   (1451)  ....GA.ATC...T..A..T..T........C..C.....T..GA.A..G 31 L1 wt      (1501)  AAAACTAAAAAGTAA (SEQ ID NO:1)
31 L1 partial (1501)  ............... (SEQ ID NO:2)
31 L1 total   (1501)  ............... (SEQ ID NO:3)
```

FIG.1D

HPV31 L1 total rebuild nucleotide and amino acid sequences.

```
        M   S   L   W       R   P   S       E   A   T       V   Y   L   P       P   V   P
  1   ATGTCTTTGT  GGAGACCATC  TGAAGCTACC  GTCTACTTGC  CACCAGTCCC

V   S   K       V   V   S   T       D   E   Y       V   T   R       T   N   I   Y
 51   AGTCTCTAAG  GTCGTCTCTA  CCGACGAATA  CGTCACCAGA  ACCAACATCT

Y   H   A       G   S   A       R   L   L   T       V   G   H       P   Y   Y
101   ACTACCACGC  TGGTTCTGCT  AGATTGTTGA  CCGTCGGTCA  CCCATACTAC

S   I   P   K       S   D   N       P   K   K       I   V   V   P       K   V   S
151   TCTATCCCAA  AGTCTGACAA  CCCAAAGAAG  ATCGTCGTCC  CAAAGGTCTC

G   L   Q       Y   R   V   F       R   V   R       L   P   D       P   N   K   F
201   TGGTTTGCAA  TACAGAGTCT  TCAGAGTCAG  ATTGCCAGAC  CCAAACAAGT

G   F   P       D   T   S       F   Y   N   P       E   T   Q       R   L   V
251   TCGGTTTCCC  AGACACCTCT  TTCTACAACC  CAGAAACCCA  AAGATTGGTC

W   A   C   V       G   L   E       V   G   R       G   Q   P   L       G   V   G
301   TGGGCTTGTG  TCGGTTTGGA  AGTCGGTAGA  GGTCAACCAT  TGGGTGTCGG

I   S   G       H   P   L   L       N   K   F       D   D   T       E   N   S   N
351   TATCTCTGGT  CACCCATTGT  TGAACAAGTT  CGACGACACC  GAAAACTCTA

R   Y   A       G   G   P       G   T   D   N       R   E   C       I   S   M
401   ACAGATACGC  TGGTGGTCCA  GGTACCGACA  ACAGAGAATG  TATCTCTATG

D   Y   K   Q       T   Q   L       C   L   L       G   C   K   P       P   I   G
451   GACTACAAGC  AAACCCAATT  GTGTTTGTTG  GGTTGTAAGC  CACCAATCGG

E   H   W       G   K   G   S       P   C   S       N   N   A       I   T   P   G
501   TGAACACTGG  GGTAAGGGTT  CTCCATGTTC  TAACAACGCT  ATCACCCCAG

D   C   P       P   L   E       L   K   N   S       V   I   Q       D   G   D
551   GTGACTGTCC  ACCATTGGAA  TTGAAGAACT  CTGTCATCCA  AGACGGTGAC
```

FIG. 2A

```
            M  V  D  T     G  F  G     A  M  D     F  T  A  L     Q  D  T
      601   ATGGTCGACA  CCGGTTTCGG  TGCTATGGAC  TTCACCGCTT  TGCAAGACAC

K  S  N     V  P  L  D     I  C  N     S  I  C     K  Y  P  D
      651   CAAGTCTAAC  GTCCCATTGG  ACATCTGTAA  CTCTATCTGT  AAGTACCCAG

Y  L  K     M  V  A     E  P  Y  G     D  T  L     F  F  Y
      701   ACTACTTGAA  GATGGTCGCT  GAACCATACG  GCGACACCTT  GTTCTTCTAC

L  R  R  E     Q  M  F     V  R  H     F  F  N  R     S  G  T
      751   TTGCGTAGAG  AACAGATGTT  CGTAAGGCAC  TTCTTCAACA  GATCCGGCAC

V  G  E     S  V  P  T     D  L  Y     I  K  G     S  G  S  T
      801   CGTAGGTGAA  TCTGTCCCAA  CCGACCTGTA  CATCAAGGGC  TCCGGTTCCA

A  T  L     A  N  S     T  Y  F  P     T  P  S     G  S  M
      851   CCGCTACCCT  GGCTAACTCC  ACCTACTTCC  CAACTCCATC  TGGCTCCATG

V  T  S  D     A  Q  I     F  N  K     P  Y  W  M     Q  R  A
      901   GTCACCTCCG  ACGCTCAGAT  CTTCAACAAG  CCATACTGGA  TGCAGCGTGC

Q  G  H     N  N  G  I     C  W  G     N  Q  L     F  V  T  V
      951   ACAGGGTCAC  AACAACGGTA  TCTGTTGGGG  TAACCAGCTG  TTCGTGACTG

V  D  T     T  R  S     T  N  M  S     V  C  A     A  I  A
     1001   TGGTCGATAC  CACGCGTTCT  ACCAACATGT  CTGTCTGTGC  TGCAATCGCT

N  S  D  T     T  F  K     S  S  N     F  K  E  Y     L  R  H
     1051   AACTCTGACA  CTACCTTCAA  GTCCTCTAAC  TTCAAGGAGT  ACCTGAGACA

G  E  E     F  D  L  Q     F  I  F     Q  L  C     K  I  T  L
     1101   TGGTGAGGAA  TTCGATCTGC  AATTCATCTT  CCAGTTGTGC  AAGATCACCC

S  A  D     I  M  T     Y  I  H  S     M  N  P     A  I  L
     1151   TGTCTGCTGA  CATCATGACC  TACATCCACA  GTATGAACCC  TGCCATCCTG

E  D  W  N     F  G  L     T  T  P     P  S  G  S     L  E  D
     1201   GAGGACTGGA  ACTTCGGTCT  GACCACTCCA  CCTTCCGGTT  CTTTGGAAGA
```

FIG.2B

```
            T  Y  R     F  V  T  S     Q  A  I     T  C  Q     K  S  A  P
1251   CACCTACAGA TTCGTCACCT CTCAAGCTAT CACCTGTCAA AAGTCTGCTC

Q  K  P     K  E  D     P  F  K  D     Y  V  F     W  E  V
1301   CACAAAAGCC AAAGGAAGAC CCATTCAAGG ACTACGTCTT CTGGGAAGTC

N  L  K  E     K  F  S     A  D  L     D  Q  F  P     L  G  R
1351   AACTTGAAGG AAAAGTTCTC TGCTGACTTG GACCAATTCC CATTGGGTAG

K  F  L     L  Q  A  G     Y  R  A     R  P  K     F  K  A  G
1401   AAAGTTCTTG TTGCAAGCTG GTTACAGAGC TAGACCAAAG TTCAAGGCTG

K  R  S     A  P  S     A  S  T  T     T  P  A     K  R  K
1451   GTAAGAGATC TGCTCCATCT GCTTCTACCA CCACCCCAGC TAAGAGAAAG

K  T  K  K     * (SEQ ID NO:4)
1501   AAGACCAAGA AGTAA (SEQ ID NO:3)
```

FIG.2C

SUMMARY OF HPV 31 SEQUENCES.

| L1 CONSTRUCT | NUCLEOTIDES | AMINO ACIDS | NUCLEOTIDE IDENTITY | AMINO ACID IDENTITY | COMMENTS |
|---|---|---|---|---|---|
| HPV 31 L1 WILD-TYPE | 1515 | 504 | | | |
| HPV 31 L1 PARTIAL REBUILD | 1515 | 504 | 92% | 100% | 121 CHANGES BETWEEN nt 697–1249 |
| HPV 31 L1 TOTAL REBUILD | 1515 | 504 | 75% | 100% | 376 CHANGES BETWEEN nt 1–1515 |

FIG.3

RESULTS FROM RADIOIMMUNOASSAY

| EXP. | L1 CONSTRUCT | PROTEIN CONCENTRATION (mg/ml) | RIA MINUS BACKGROUND (cpm/ml) | 31 L1 VLP*/ mg protein (cpm/mg) | AVERAGE (cpm/mg) | RATIO (Ave/Ave) |
|---|---|---|---|---|---|---|
| 1 | 31 WILD-TYPE | 1.64 | 414 | 252 | 460 | 1 (31 wt/31 wt) |
|   |   | 1.62 | 987 | 609 |   |   |
|   |   | 1.82 | 904 | 497 |   |   |
|   |   | 1.76 | 844 | 480 |   |   |
| 1 | 31 PARTIAL REBUILD | 1.67 | 5061 | 3031 | 3158 | 6.9 (31 PARTIAL/31 wt) |
|   |   | 1.55 | 5091 | 3285 |   |   |
| 2 | 31 PARTIAL REBUILD | 2.27 | 3901 | 1719 | 2095 | 1 (31 PARTIAL/31 PARTIAL) |
|   |   | 2.27 | 4081 | 1798 |   |   |
|   |   | 2.38 | 7135 | 2998 |   |   |
|   |   | 2.38 | 4428 | 1861 |   |   |
| 2 | 31 TOTAL REBUILD | 2.07 | 6628 | 3202 | 3645 | 1 (31 TOTAL/31 PARTIAL) |
|   |   | 2.07 | 8461 | 4087 |   |   |

FIG.5

OPTIMIZED EXPRESSION OF HPV 31 L1 IN YEAST

CROSS-REFERENCE TO RELATED APPLICATIONS

This application is a divisional of U.S. Ser. No. 10/551,057, filed Sep. 26, 2005, now U.S. Pat. No. 7,276,243, which is a §371 National Stage Application of PCT/US2004/008677, international filing date of Mar. 19, 2004, which claims the benefit of U.S. Provisional Application No. 60/457,172, filed Mar. 24, 2003, now expired.

FIELD OF THE INVENTION

The present invention relates generally to the therapy of human papillomavirus (HPV). More specifically, the present invention relates to synthetic polynucleotides encoding HPV31 L1 protein, and to recombinant vectors and hosts comprising said polynucleotides. This invention also relates to HPV31 virus-like particles (VLPs) and to their use in vaccines and pharmaceutical compositions for preventing and treating HPV.

BACKGROUND OF THE INVENTION

There are more than 80 types of human papillomavirus (HPV), many of which have been associated with a wide variety of biological phenotypes, from benign proliferative warts to malignant carcinomas (for review, see McMurray et al., *Int. J. Exp. Pathol.* 82(1): 15-33 (2001)). HPV6 and HPV11 are the types most commonly associated with benign warts, nonmalignant condylomata acuminate and/or low-grade dysplasia of the genital or respiratory mucosa. HPV16 and HPV18 are the high-risk types most frequently associated with in situ and invasive carcinomas of the cervix, vagina, vulva and anal canal. More than 90% of cervical carcinomas are associated with infections of HPV16, HPV18 or the less prevalent oncogenic types HPV31, -33, -45, -52 and -58 (Schiffman et al., *J. Natl. Cancer Inst.* 85(12): 958-64 (1993)). The observation that HPV DNA is detected in 90-100% of cervical cancers provides strong epidemiological evidence that HPVs cause cervical carcinoma (see Bosch et al., *J. Clin. Pathol.* 55: 244-265 (2002)).

Papillomaviruses are small (50-60 nm), nonenveloped, icosahedral DNA viruses that encode up to eight early and two late genes. The open reading frames (ORFs) of the viral genomes are designated E1 to E7, and L1 and L2, where "E" denotes early and "L" denotes late. L1 and L2 code for virus capsid proteins, while the E genes are associated with functions such as viral replication and cellular transformation.

The L1 protein is the major capsid protein and has a molecular weight of 55-60 kDa. The L2 protein is a minor capsid protein. Immunological data suggest that most of the L2 protein is internal to the L1 protein. Both the L1 and L2 proteins are highly conserved among different papillomaviruses.

Expression of the L1 protein or a combination of the L1 and L2 proteins in yeast, insect cells, mammalian cells or bacteria leads to self-assembly of virus-like particles (VLPs) (for review, see Schiller and Roden, in *Papillomavirus Reviews: Current Research on Papillomaviruses*; Lacey, ed. Leeds, UK: Leeds Medical Information, pp 101-12 (1996)). VLPs are morphologically similar to authentic virions and are capable of inducing high titers of neutralizing antibodies upon administration into an animal or a human. Because VLPs do not contain the potentially oncogenic viral genome, they present a safe alternative to use of live virus in HPV vaccine development (for review, see Schiller and Hidesheim, *J. Clin. Virol.* 19: 67-74 (2000)). For this reason, the L1 and L2 genes have been identified as immunological targets for the development of prophylactic and therapeutic vaccines for HPV infection and disease.

HPV vaccine development and commercialization have been hindered by difficulties associated with obtaining high expression levels of capsid proteins in successfully transformed host organisms, limiting the production of purified protein. Therefore, despite the identification of wild-type nucleotide sequences encoding HPV L1 proteins such as HPV31 L1 proteins (Goldsborough et al., Virology 171(1): 306-311 (1989), it would be highly desirable to develop a readily renewable source of crude HPV proteins that utilizes HPV31 L1-encoding nucleotide sequences that are optimized for expression in the intended host cell. Additionally, it would be useful to produce large quantities of HPV31 L1 VLPs having the immunity-conferring properties of the native proteins for use in vaccine development.

SUMMARY OF THE INVENTION

The present invention relates to compositions and methods to elicit or enhance immunity to the protein products expressed by HPV31 L1 genes, which have been associated with cervical cancer. Specifically, the present invention provides polynucleotides encoding HPV31 L1 protein, wherein said polynucleotides are free from internal transcription termination signals that are recognized by yeast. Also provided are synthetic polynucleotides encoding HPV31 L1 wherein the polynucleotides have been codon-optimized for high level expression in a yeast cell. The present invention further provides HPV31 virus-like particles (VLPs) and discloses use of said VLPs in immunogenic compositions and vaccines for the prevention and/or treatment of HPV disease or HPV-associated cancer.

The present invention relates to synthetic DNA molecules encoding the HPV31 L1 protein. In one aspect of the invention, the nucleotide sequence of the synthetic molecule is altered to eliminate transcription termination signals that are recognized by yeast. In another aspect, the codons of the synthetic molecules are designed so as to use the codons preferred by a yeast cell. The synthetic molecules may be used as a source of HPV31 L1 protein, which may self-assemble into VLPs. Said VLPs may be used in a VLP-based vaccine.

A particular embodiment of the present invention comprises a synthetic nucleic acid molecule which encodes the HPV31 L1 protein as set forth in SEQ ID NO:4, said nucleic acid molecule comprising a sequence of nucleotides as set forth in SEQ ID NO:2 or SEQ ID NO:3.

As stated above, provided herein are synthetic polynucleotides encoding the HPV31 L1 gene which are free from transcription termination signals that are recognized by yeast. This invention also provides synthetic polynucleotides encoding HPV 31 L1 as described, which are further altered so as to contain codons that are preferred by yeast cells.

Also provided are recombinant vectors and recombinant host cells, both prokaryotic and eukaryotic, which contain the nucleic acid molecules disclosed throughout this specification.

The present invention relates to a process for expressing an HPV31 L1 protein in a recombinant host cell, comprising: (a) introducing a vector comprising a nucleic acid encoding an HPV31 L1 protein into a yeast host cell; wherein the nucleic acid molecule is free from internal transcription termination signals that are recognized by yeast and; (b) culturing the yeast host cell under conditions which allow expression of said HPV31 L1 protein.

The present invention further relates to a process for expressing an HPV31 L1 protein in a recombinant host cell, comprising: (a) introducing a vector comprising a nucleic acid encoding an HPV31 L1 protein into a yeast host cell; wherein the nucleic acid molecule is codon-optimized for optimal expression in the yeast host cell and; (b) culturing the yeast host cell under conditions which allow expression of said HPV31 L1 protein.

In preferred embodiments, the nucleic acid comprises a sequence of nucleotides as set forth in SEQ ID NO:2 or SEQ ID NO:3.

This invention also relates to HPV31 virus-like particles (VLPs), methods of producing HPV31 VLPs, and methods of using HPV31 VLPs.

In a preferred embodiment of the invention, the HPV31 VLPs are produced in yeast. In a further preferred embodiment, the yeast is selected from the group consisting of: *Saccharomyces cerevisiae, Hansenula polymorpha, Pichia pastoris, Kluyvermyces fragilis, Kluveromyces lactis,* and *Schizosaccharomyces pombe.*

Another aspect of this invention is an HPV31 VLP, which comprises an HPV31 L1 protein produced by a HPV31 L1 gene which is free from transcription termination signals that are recognized by yeast.

Yet another aspect of this invention is an HPV31 VLP, which comprises an HPV31 L1 protein produced by a codon-optimized HPV31 L1 gene. In a preferred embodiment of this aspect of the invention, the codon-optimized HPV31 L1 gene consists essentially of a sequence of nucleotides as set forth in SEQ ID NO:2 or SEQ ID NO:3.

This invention also provides a method for inducing an immune response in an animal comprising administering HPV31 virus-like particles to the animal. In a preferred embodiment, the HPV31 VLPs are produced by a codon-optimized gene. In a further preferred embodiment, the HPV31 VLPs are produced by a gene that is free from transcription termination sequences that are recognized by yeast.

Yet another aspect of this invention is a method of preventing or treating HPV-associated cervical cancer comprising administering to a mammal a vaccine comprising HPV31 VLPs. In a preferred embodiment of this aspect of the invention, the HPV31 VLPs are produced in yeast.

This invention also relates to a vaccine comprising HPV31 virus-like particles (VLPs).

In an alternative embodiment of this aspect of the invention, the vaccine further comprises VLPs of at least one additional HPV type. In a preferred embodiment, the at least one additional HPV type is selected from the group consisting of: HPV6, HPV11, HPV16, HPV18, HPV33, HPV35, HPV39, HPV45, HPV51, HPV52, HPV55, HPV56, HPV58, HPV59, and HPV68.

This invention also relates to pharmaceutical compositions comprising HPV 31 virus-like particles. Further, this invention relates to pharmaceutical compositions comprising HPV31 VLPs and VLPs of at least one additional HPV type. In a preferred embodiment, the at least one additional HPV type is selected from the group consisting of: HPV6, HPV11, HPV16, HPV18, HPV33, HPV35, HPV39, HPV45, HPV51, HPV52, HPV55, HPV56, HPV58, HPV59, and HPV68.

As used throughout the specification and in the appended claims, the singular forms "a," "an," and "the" include the plural reference unless the context clearly dictates otherwise.

As used throughout the specification and appended claims, the following definitions and abbreviations apply:

The term "promoter" refers to a recognition site on a DNA strand to which the RNA polymerase binds. The promoter forms an initiation complex with RNA polymerase to initiate and drive transcriptional activity. The complex can be modified by activating sequences termed "enhancers" or "upstream activating sequences" or inhibiting sequences termed "silencers".

The term "vector" refers to some means by which DNA fragments can be introduced into a host organism or host tissue. There are various types of vectors including plasmid, virus (including adenovirus), bacteriophages and cosmids.

The designation "31 L1 wild-type sequence" refers to the HPV31 L1 sequence disclosed herein as SEQ ID NO:1. Although the HPV 31 L1 wild-type sequence has been described previously, it is not uncommon to find minor sequence variations between DNAs obtained from clinical isolates. Therefore, a representative HPV31 L1 wild-type sequence was isolated from clinical samples previously shown to contain HPV 31 DNA (see EXAMPLE 1). The 31 L1 wild-type sequence was used as a reference sequence to compare the codon-optimized HPV 31 L1 sequences disclosed herein (see FIG. 1).

The designation "31 L1 partial rebuild" refers to a construct, disclosed herein (SEQ ID NO:2), in which the HPV31 L1 nucleotide sequence was partially rebuilt to contain yeast-preferred codons for optimal expression in yeast. The 31 L1 partial rebuild comprises alterations in the middle portion of the HPV 31 L1 wild-type nucleotide sequence (nucleotides 697-1249). The complete HPV 31 L1 sequence was also rebuilt with yeast-preferred codons, which is referred to herein as the "31 L1 total rebuild" (SEQ ID NO:3).

The term "effective amount" means sufficient vaccine composition is introduced to produce the adequate levels of the polypeptide, so that an immune response results. One skilled in the art recognizes that this level may vary.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

The term "mammalian" refers to any mammal, including a human being.

"VLP" or "VLPs" mean(s) virus-like particle or virus-like particles.

"Synthetic" means that the HPV31 L1 gene has been modified so that it contains a sequence of nucleotides that is not the same as the sequence of nucleotides present in the naturally occurring wild-type HPV31 L1 gene. As stated above, synthetic molecules are provided herein comprising a sequence of nucleotides that are altered to eliminate transcription termination signals recognized by yeast. Also provided herein are synthetic molecules comprising codons that are preferred for expression by yeast cells. The synthetic molecules provided herein encode the same amino acid sequences as the wild-type HPV31 L1 gene.

BRIEF DESCRIPTION OF THE DRAWINGS

FIG. 1 is a sequence alignment showing nucleotides that were altered in the partial (SEQ ID NO:2) and total rebuild (SEQ ID NO:3) 31 L1 genes (See EXAMPLE 2). The reference sequence is the 31 L1 wild-type sequence (SEQ ID NO:1; see EXAMPLE 1). Nucleotides in the 31 L1 partial and total rebuild sequences that are identical to the reference sequence are indicated with dots. Altered nucleotides are indicated at their corresponding location. Nucleotide number is contained within the parentheses.

FIG. 2 shows the 31 L1 total rebuild nucleotide (SEQ ID NO:3) and amino acid sequences (SEQ ID NO:4). The nucleotide number is indicated on the left.

FIG. 3 summarizes the changes between the three HPV 31 L1 sequence constructs, which are listed on the left. The fourth column indicates the percent nucleotide identity between the indicated construct and the 31 L1 wild-type sequence and the fifth column indicates the amino acid identity. The last column indicates the number of nucleotides that were altered to yeast-preferred codon sequences and the region where the alterations were made.

FIG. 5 shows a portion of the data from two capture radioimmunoassay (RIA) experiments in counts per minute (cpm)/mg total protein (see EXAMPLE 7). Cpm obtained in the RIA are a relative indicator of HPV 31 L1 VLPs. The RIA data demonstrate increased 31 L1 VLP expression in yeast protein extracts from yeast-preferred codon rebuilt gene sequences.

DETAILED DESCRIPTION OF THE INVENTION

Figure 4:
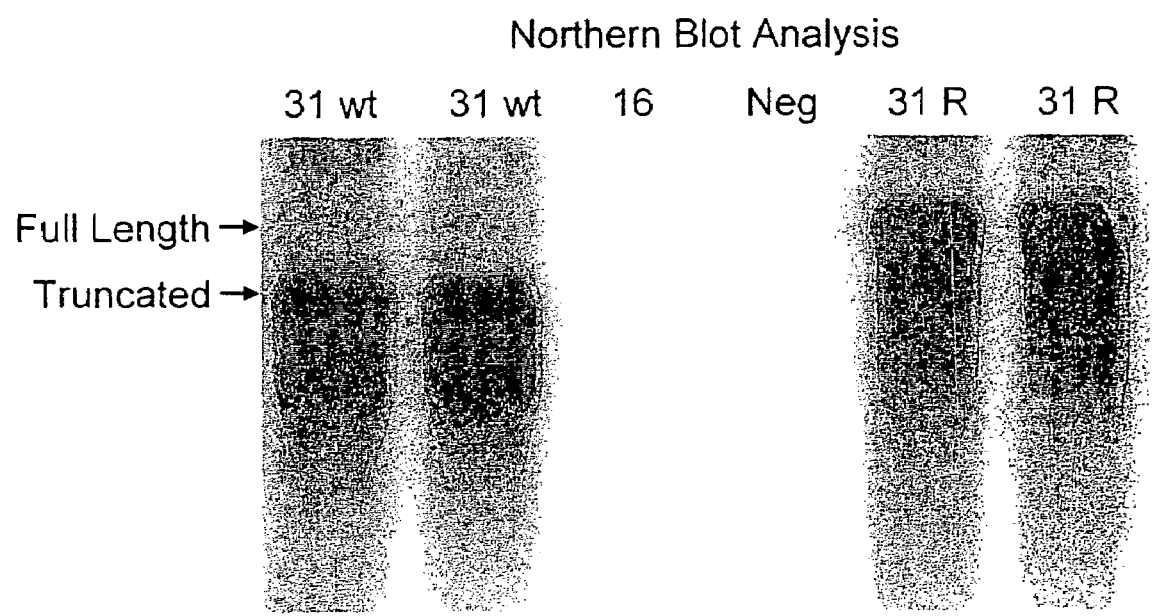
FIG. 4 shows a Northern blot probed specifically for HPV 31 L1 under high stringency (see EXAMPLE 4). Arrows on the left indicate the position of the HPV 31 L1 full length and truncated transcripts. Lanes labeled "31 wt" are from the same RNA preparation of yeast containing 31 L1 wild-type sequences. The lane labeled "16" contains RNA from HPV16, which is not recognized by the HPV 31 L1 probe because of the high stringency conditions. The lane labeled "Neg" is a yeast extract containing no L1 coding sequences. Lanes labeled "31 R" are from RNA of two separate isolated colonies expressing the 31 L1 partial rebuild sequence.

The majority of cervical carcinomas are associated with infections of specific oncogenic types of human papillomavirus (HPV). The present invention relates to compositions and methods to elicit or enhance immunity to the protein products expressed by genes of oncogenic HPV types. Specifically, the present invention provides polynucleotides encoding HPV31 L1 and HPV31 virus-like particles (VLPs) and discloses use of said polynucleotides and VLPs in immunogenic compositions and vaccines for the prevention and/or treatment of HPV-associated cancer.

The wild-type HPV31 L1 nucleotide sequence has been reported (Goldsborough et al., *Virology* 171(1): 306-311 (1989); Genbank Accession # J04353). The present invention provides synthetic DNA molecules encoding the HPV31 L1 protein. The synthetic molecules of the present invention comprise a sequence of nucleotides, wherein some of the nucleotides have been altered so as to eliminate transcription termination signals that are recognized by yeast. In alternative embodiments, the codons of the synthetic molecules are designed so as to use the codons preferred by a yeast cell for high-level expression. The synthetic molecules may be used as a source of HPV31 L1 protein, which may self-assemble into VLPs. Said VLPs may be used in a VLP-based vaccine to provide effective immunoprophylaxis against papillomavirus infection through neutralizing antibody and cell-mediated immunity. Such VLP-based vaccines are also useful for treatment of already established HPV infections.

Expression of HPV VLPs in yeast cells offers the advantages of being cost-effective and easily adapted to large-scale growth in fermenters. However, many HPV L1 proteins, including HPV31 L1 (see EXAMPLE 4), are expressed at low levels in yeast cells. It has been determined in accordance with the present invention that low level expression of HPV31 L1 is due to truncation of the mRNA transcript resulting from the presence of transcription termination signals that are recognized by yeast. By altering the HPV31 L1 DNA to eliminate any potential sequences resembling yeast transcription termination sites, it is possible to facilitate the transcription of full-length mRNA resulting in increased HPV31 L1 protein expression.

Accordingly, in some embodiments of this invention, alterations have been made to the HPV31 L1 DNA to eliminate any potential sequences resembling yeast transcription termination signals. These alterations allow expression of the full-length HPV31 transcript, as opposed to a truncated transcript (see EXAMPLE 4), improving expression yield.

As noted above, synthetic DNAs of the present invention comprise alterations from the wild-type HPV31 L1 sequence that were made to eliminate yeast-recognized transcription termination sites. One of skill in the art will recognize that additional DNA molecules can be constructed that encode the HPV31 L1 protein, but do not contain yeast transcription termination sites. Techniques for finding yeast transcription termination sequences are well known in the art. Transcription termination and 3' end formation of yeast mRNAs requires the presence of three signals: (1) an efficiency element such as TATATA or related sequences, which enhances the efficiency of positioning elements located downstream; (2) positioning element(s), which determine the location of the poly(A) site and (3) the polyadenylation site (usually Py(A)n).

The scientific literature is replete with descriptions of sequences that encode yeast transcription termination signals. See, for example, Guo and Sherman, *Trends Biochem. Sci.* 21: 477-481 (1986); Guo and Sherman, *Mol. Cell. Biol.* 16(6): 2772-2776 (1996); Zaret et al, *Cell* 28:563-573 (1982); Henikoff et al, *Cell* 33:607-614 (1983); Thalenfeld et al, *J. Biol. Chem.* 258(23):14065-14068 (1983); Zaret et al, *J. Mol. Biol.* 176:107-135 (1984); Heidmann et al, *Mol. Cell. Biol* 14:4633-4642 (1984); and Russo, *Yeast* 11:447-453 (1985). Therefore, one of skill in the art would have no difficulty determining which sequences to avoid in order to construct a synthetic HPV31 L1 gene that produces a full-length mRNA transcript in accordance with the present invention. Additionally, assays and procedures to assess whether a yeast transcription termination sequence is present within the synthetic sequence are well established in the art, so that an ordinary skilled artisan would be able to determine if a constructed HPV31 L1 sequence comprises termination sequences that need to be eliminated.

As described above, the present invention relates to a nucleic acid molecule encoding HPV type 31 L1 protein, the nucleic acid molecule being free from internal transcription termination signals which are recognized by yeast. In exemplary embodiments of the invention, the synthetic nucleic acid molecules comprise a sequence of nucleotides as set forth in SEQ ID NO:2 or SEQ ID NO:3.

In alternative embodiments of the present invention, HPV31 L1 gene sequences are "optimized" for high level expression in a yeast cellular environment. Codon-optimized HPV31 L1 genes contemplated by the present invention include synthetic molecules encoding HPV31 L1 that are free from internal transcription termination signals which are recognized by yeast, further comprising at least one codon that is codon-optimized for high level expression in yeast cells.

A "triplet" codon of four possible nucleotide bases can exist in over 60 variant forms. Because these codons provide the message for only 20 different amino acids (as well as transcription initiation and termination), some amino acids can be coded for by more than one codon, a phenomenon known as codon redundancy. For reasons not completely understood, alternative codons are not uniformly present in the endogenous DNA of differing types of cells. Indeed, there appears to exist a variable natural hierarchy or "preference" for certain codons in certain types of cells. As one example, the amino acid leucine is specified by any of six DNA codons including CTA, CTC, CTG, CTT, TTA, and TTG. Exhaustive analysis of genome codon frequencies for microorganisms has revealed endogenous DNA of *E. coli* most commonly contains the CTG leucine-specifying codon, while the DNA of yeasts and slime molds most commonly includes a TTA leucine-specifying codon. In view of this hierarchy, it is generally believed that the likelihood of obtaining high levels of expression of a leucine-rich polypeptide by an *E. coli* host will depend to some extent on the frequency of codon use. For example, it is likely that a gene rich in TTA codons will be poorly expressed in *E. coli*, whereas a CTG rich gene will probably be highly expressed in this host. Similarly, a preferred codon for expression of a leucine-rich polypeptide in yeast host cells would be TTA.

The implications of codon preference phenomena on recombinant DNA techniques are manifest, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide an optimal form of foreign genetic material for practice of recombinant DNA techniques. Thus, one aspect of this invention is an HPV31 L1 gene that is codon-optimized for expression in a yeast cell. In a preferred embodiment of this invention, it has been found that the use of alternative codons encoding the same protein sequence may remove the constraints on expression of HPV31 L1 proteins by yeast cells.

In accordance with this invention, HPV31 L1 gene segments were converted to sequences having identical translated sequences but with alternative codon usage as described by Sharp and Cowe (Synonymous Codon Usage in *Saccharomyces cerevisiae*. Yeast 7: 657-678 (1991)), which is hereby incorporated by reference. The methodology generally consists of identifying codons in the wild-type sequence that are not commonly associated with highly expressed yeast genes and replacing them with optimal codons for high expression in yeast cells. The new gene sequence is then inspected for undesired sequences generated by these codon replacements (e.g., "ATTTA" sequences, inadvertent creation of intron splice recognition sites, unwanted restriction enzyme sites, etc.). Undesirable sequences are eliminated by substitution of the existing codons with different codons coding for the same amino acid. The synthetic gene segments are then tested for improved expression.

The methods described above were used to create synthetic gene segments for HPV31 L1, resulting in a gene comprising codons optimized for high level expression. While the above procedure provides a summary of our methodology for designing codon-optimized genes for use in HPV vaccines, it is understood by one skilled in the art that similar vaccine efficacy or increased expression of genes may be achieved by minor variations in the procedure or by minor variations in the sequence.

Accordingly, the present invention relates to a synthetic polynucleotide comprising a sequence of nucleotides encoding an HPV31 L1 protein, or a biologically active fragment or mutant form of an HPV31 L1 protein, the polynucleotide sequence comprising codons optimized for expression in a yeast host. Said mutant forms of the HPV31 L1 protein include, but are not limited to: conservative amino acid substitutions, amino-terminal truncations, carboxy-terminal truncations, deletions, or additions. Any such biologically active fragment and/or mutant will encode either a protein or protein fragment which at least substantially mimics the immunological properties of the HPV31 L1 protein as set forth in SEQ ID NO:4. The synthetic polynucleotides of the present invention encode mRNA molecules that express a functional HPV31 L1 protein so as to be useful in the development of a therapeutic or prophylactic HPV vaccine.

One aspect of this invention is a codon-optimized nucleic acid molecule which encodes the HPV31 L1 protein as set forth in SEQ ID NO:4, said nucleic acid molecule comprising a sequence of nucleotides as set forth in SEQ ID NO:2.

Another aspect of this invention is a codon-optimized nucleic acid molecule which encodes the HPV31 L1 protein as set forth in SEQ ID NO:4, said nucleic acid molecule comprising a sequence of nucleotides as set forth in SEQ ID NO:3.

The present invention also relates to recombinant vectors and recombinant host cells, both prokaryotic and eukaryotic, which contain the nucleic acid molecules disclosed throughout this specification.

The synthetic HPV31 DNA or fragments thereof constructed through the methods described herein may be recombinantly expressed by molecular cloning into an expression vector containing a suitable promoter and other appropriate transcription regulatory elements, and transferred into prokaryotic or eukaryotic host cells to produce recombinant HPV31 L1. Techniques for such manipulations are described in the art (Sambrook et al. Molecular Cloning: A Laboratory Manual; Cold Spring Harbor Laboratory Press, Cold Spring Harbor, N.Y., (1989); Current Protocols in Molecular Biology, Ausubel et al., Green Pub. Associates and Wiley-Interscience, New York (1988); Yeast Genetics: A Laboratory Course Manual, Rose et al., Cold Spring Harbor Laboratory, Cold Spring Harbor, N.Y., (1990), which are hereby incorporated by reference in their entirety).

Thus, the present invention further relates to a process for expressing an HPV31 L1 protein in a recombinant host cell, comprising: (a) introducing a vector comprising a nucleic acid encoding an HPV31 L1 protein into a yeast host cell; wherein the nucleic acid molecule is codon-optimized for optimal expression in the yeast host cell and; (b) culturing the yeast host cell under conditions which allow expression of said HPV31 L1 protein.

The present invention also relates to a process for expressing an HPV31 L1 protein in a recombinant host cell, comprising: (a) introducing a vector comprising a nucleic acid encoding an HPV31 L1 protein into a yeast host cell; wherein the nucleic acid molecule is free from internal transcription termination signals which are recognized by yeast and; (b) culturing the yeast host cell under conditions which allow expression of said HPV31 L1 protein.

This invention further relates to a process for expressing an HPV31 L1 protein in a recombinant host cell, comprising: (a) introducing a vector comprising a nucleic acid as set forth in SEQ ID NO:2 or SEQ ID NO:3 into a yeast host cell; and, (b) culturing the host cell under conditions which allow expression of said HPV31 L1 protein.

The synthetic genes of the present invention can be assembled into an expression cassette that comprises sequences designed to provide efficient expression of the HPV58 L1 protein in the host cell. The cassette preferably contains the synthetic gene, with related transcriptional and translations control sequences operatively linked to it, such as a promoter, and termination sequences. In a preferred embodiment, the promoter is the *S. cerevisiae* GAL1 promoter, although those skilled in the art will recognize that any of a number of other known yeast promoters such as the GAL10, GAL7, ADH1, TDH3 or PGK promoters, or other eukaryotic gene promoters may be used. A preferred transcriptional terminator is the *S. cerevisiae* ADH1 terminator, although other known transcriptional terminators may also be used. The combination of GAL1 promoter—ADH1 terminator is particularly preferred.

Another aspect of this invention is an HPV31 virus-like particle (VLP), methods of producing HPV31 VLPs, and methods of using HPV31 VLPs. VLPs can self-assemble when L1, the major capsid protein of human and animal papillomaviruses, is expressed in yeast, insect cells, mammalian cells or bacteria (for review, see Schiller and Roden, in *Papillomavirus Reviews: Current Research on Papillomaviruses*; Lacey, ed. Leeds, UK: Leeds Medical Information, pp 101-12 (1996)). Morphologically indistinct HPV VLPs can also be produced by expressing a combination of the L1 and L2 capsid proteins. VLPs are composed of 72 pentamers of L1 in a T=7 icosahedral structure (Baker et al., *Biophys. J.* 60(6): 1445-56 (1991)).

VLPs are morphologically similar to authentic virions and are capable of inducing high titres of neutralizing antibodies upon administration into an animal. Immunization of rabbits (Breitburd et al., *J. Virol.* 69(6): 3959-63 (1995)) and dogs (Suzich et al., *Proc. Natl. Acad. Sci. USA* 92(25): 11553-57 (1995)) with VLPs was shown to both induce neutralizing antibodies and protect against experimental papillomavirus infection. However, because the VLPs do not contain the potentially oncogenic viral genome and can self-assemble from a single gene, they present a safe alternative to use of live virus in HPV vaccine development (for review, see Schiller and Hidesheim, *J. Clin. Virol.* 19: 67-74 (2000)).

Thus, the present invention relates to virus-like particles comprised of recombinant L1 protein or recombinant L1+L2 proteins of HPV31.

In a preferred embodiment of the invention, the HPV31 VLPs are produced in yeast. In a further preferred embodiment, the yeast is selected from the group consisting of: *Saccharomyces cerevisiae, Hansenula polymorpha, Pichia pastoris, Kluyvermyces fragilis, Kluveromyces lactis*, and *Schizosaccharomyces pombe*.

Another aspect of this invention is an HPV31 VLP, which comprises an HPV31 L1 protein produced by a HPV31 L1 gene that is free from internal transcription termination signals that are recognized by yeast.

Yet another aspect of this invention is an HPV31 VLP which comprises an HPV31 L1 protein produced by a codon-optimized HPV31 L1 gene. In a preferred embodiment of this aspect of the invention, the codon-optimized HPV31 L1 gene consists essentially of a sequence of nucleotides as set forth in SEQ ID NO:2 or SEQ ID NO:3.

Yet another aspect of this invention is a method of producing HPV31 VLPs, comprising: (a) transforming yeast with a recombinant DNA molecule encoding HPV31 L1 protein or HPV31 L1+L2 proteins; (b) cultivating the transformed yeast under conditions that permit expression of the recombinant DNA molecule to produce the recombinant HPV31 protein; and (c) isolating the recombinant HPV31 protein to produce HPV31 VLPs.

In a preferred embodiment of this aspect of the invention, the yeast is transformed with a HPV31 L1 gene that is free from transcription termination signals that are recognized by yeast. In another preferred embodiment, the yeast is transformed with a codon-optimized HPV31 L1 gene to produce HPV31 VLPs. In a particularly preferred embodiment, the codon-optimized HPV31 L1 gene consists essentially of a sequence of nucleotides as set forth in SEQ ID NO:2 or SEQ ID NO:3.

This invention also provides a method for inducing an immune response in an animal comprising administering HPV31 virus-like particles to the animal. In a preferred embodiment, the HPV31 VLPs are produced by a gene that is free from internal transcription termination sequences that are recognized by yeast. In a further preferred embodiment, the HPV31 VLPs are produced by a codon-optimized gene.

Yet another aspect of this invention is a method of preventing or treating HPV-associated cervical cancer comprising administering to a mammal a vaccine comprising HPV31 VLPs. In a preferred embodiment of this aspect of the invention, the HPV31 VLPs are produced in yeast.

This invention also relates to a vaccine comprising HPV31 virus-like particles (VLPs).

In an alternative embodiment of this aspect of the invention, the vaccine further comprises VLPs of at least one additional HPV type. In a preferred embodiment, the at least one additional HPV type is selected from the group consisting of: HPV6, HPV11, HPV16, HPV18, HPV33, HPV35, HPV39, HPV45, HPV51, HPV52, HPV55, HPV56, HPV58, HPV59, and HPV68.

In a preferred embodiment of this aspect of the invention, the vaccine further comprises HPV16 VLPs.

In another preferred embodiment of the invention, the vaccine further comprises HPV16 VLPs and HPV18 VLPs.

In yet another preferred embodiment of the invention, the vaccine further comprises HPV6 VLPs, HPV11 VLPs, HPV16 VLPs and HPV18 VLPs.

This invention also relates to pharmaceutical compositions comprising HPV 31 virus-like particles. Further, this invention relates to pharmaceutical compositions comprising HPV31 VLPs and VLPs of at least one additional HPV type. In a preferred embodiment, the at least one additional HPV type is selected from the group consisting of: HPV6, HPV11, HPV16, HPV18, HPV33, HPV35, HPV39, HPV45, HPV51, HPV52, HPV55, HPV56, HPV58, HPV59, and HPV68.

Vaccine compositions of the present invention may be used alone at appropriate dosages defined by routine testing in order to obtain optimal inhibition of HPV31 infection while minimizing any potential toxicity. In addition, co-administration or sequential administration of other agents may be desirable.

The amount of virus-like particles to be introduced into a vaccine recipient will depend on the immunogenicity of the expressed gene product. In general, an immunologically or prophylactically effective dose of about 10 µg to 100 µg, and preferably about 20 µg to 60 µg of VLPs is administered directly into muscle tissue. Subcutaneous injection, intradermal introduction, impression though the skin, and other modes of administration such as intraperitoneal, intravenous, or inhalation delivery are also contemplated. It is also contemplated that booster vaccinations may be provided. Parenteral administration, such as intravenous, intramuscular, subcutaneous or other means of administration with adjuvants such as alum or Merck alum adjuvant, concurrently with or subsequent to parenteral introduction of the vaccine of this invention is also advantageous.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLE 1

Determination of a Representative HPV 31 L1 Sequence

The HPV 31 L1 wild-type sequence has been described previously (Goldsborough et al., *Virology* 171(1): 306-311 (1989); Genbank Accession # J04353). It is not uncommon, however, to find minor sequence variations between DNAs obtained from clinical isolates. To isolate a representative HPV31 L1 wild-type sequence, DNA was isolated from three clinical samples previously shown to contain HPV 31 DNA. HPV 31 L1 sequences were amplified in a polymerase chain reaction (PCR) using Taq DNA polymerase and the following primers: HPV 31 L1 F 5'-CGT CGA CGT AAA CGT GTA TCA TAT TTT TTT ACA G-3' (SEQ ID NO:5) and HPV 31 L1 B 5'-CAG ACA CAT GTA TTA CAT ACA CAA C-3' (SEQ ID NO:6). The amplified products were electrophoresed on agarose gels and visualized by ethidium bromide staining. The ~1500 bp L1 bands were excised and DNA purified using the QIA quick PCR purification kit (Qiagen, Hilden, Germany). The DNA was then ligated to the TA cloning vector, pCR-II (Invitrogen Corp., Carlsbad, Calif.), *E. coli* transformed, and plated on LB agar with ampicillin plus IPTG and X-gal for blue/white colony selection. The plates were inverted and incubated for 16 hours at 37° C. White colonies were cultured in LB medium with ampicillin, shaking at 37° C. for 16 hours, and minipreps were performed to extract the plasmid DNA.

To demonstrate the presence of the L1 gene in the plasmid, restriction endonuclease digestions were conducted and viewed by agarose gel electrophoresis and ethidium bromide staining. DNA sequencing was performed on plasmids containing cloned L1 from each of the three clinical isolates. DNA and translated amino acid sequences were compared with one another and the Genbank HPV 31 L1 sequences. Sequence analysis of the three clinical isolates revealed that no sequence was identical to the Genbank sequence. The pCR-II-HPV 31L1/81 clone was chosen to be the representative 31 L1 sequence and is referred to herein as the "31 L1 wild-type sequence" (SEQ ID NO:1, see FIG. 1). The sequence chosen as 31 L1 wild-type contained one silent substitution at nucleotide 1266 and a change from a C to a G at nucleotide 1295, altering the encoded amino acid from threonine to serine. The 31 L1 partial and total rebuilt genes (SEQ ID NOs: 2 and 3, respectively) also encode a serine at this location (see FIG. 1). In all cases, the amino acid sequences are identical. Nucleotides were changed in the rebuilt constructs to encode amino acids using yeast-preferred codon sequences and to eliminate potential transcription termination signals (see EXAMPLE 2).

The 31 L1 wild-type sequence was amplified using the LS-101 5'-CTC AGA TCT CAC AAA ACA AAA TGT CTC TGT GGC GGC CTA GC-3' (SEQ ID NO:7) and LS-102 5'-GAC AGA TCT TAC TTT TTA GTT TTT TTA CGT TTT GCT GG-3' (SEQ ID NO:8) primers to add BglII extensions. PCR was performed using Vent™ DNA polymerase. The PCR product was visualized by ethidium bromide staining of an agarose gel. The ~1500 bp band was excised and DNA purified using the QIAEX II gel extraction kit (Qiagen). The PCR product was then digested with BglII at 37° C. for 2 hours and purified using the QIA quick PCR purification kit. The BglII digested 31 L1 PCR product was ligated to BamHI digested pGAL110 and DH5 *E. coli* were transformed. Colonies were screened by PCR for the HPV 31 L1 insert in the correct orientation. Sequence and orientation were confirmed by DNA sequencing. The selected clone was named pGAL110-HPV 31L1 #2.

Maxiprep DNA was then prepared and *Saccharomyces cerevisiae* were made competent and transformed. The yeast transformation was plated in Leu⁻ sorbitol top-agar on Leu⁻ sorbitol plates and incubated inverted for 3-5 days at 30° C. Colonies were picked and streaked for isolation on Leu⁻ sorbitol plates. To induce L1 transcription and protein expression, isolated colonies were subsequently grown in 5 ml of 5×Leu⁻ Ade⁻ sorbitol with 1.6% glucose and 4% galactose in rotating tube cultures at 30° C.

EXAMPLE 2

Yeast Codon Optimization

Yeast-preferred codons have been described (Sharp and Cowe, *Yeast* 7: 657-678 (1991)). Initially, the middle portion of HPV 31 L1, representing nucleotides 697-1249, was rebuilt utilizing yeast-preferred codons. The strategy employed to rebuild was to design long overlapping sense and antisense oligomers that span the region to be rebuilt, substituting nucleotides with yeast-preferred codon sequences while maintaining the same amino acid sequence. These oligomers were used in place of template DNA in the PCR reaction. Additional amplification primers were designed and used to amplify the rebuilt sequences from template oligomers with Pfu DNA polymerase (Stratagene, La Jolla, Calif.). The optimal conditions for amplification were section-specific; however, most employed a program resembling the following: an initial denaturation step of 94° C. for 1 minute, followed by 15-25 cycles of 95° C. for 30 sec denature, 55° C. for 30 sec anneal, 72° C. for 3.5 minutes extension, followed by a 72° C. for 10 minute final extension and 4° C. hold.

PCR products were examined by agarose gel electrophoresis. Bands of the appropriate size were excised and the DNA was gel purified. The amplified fragments were then used as template to assemble the 552 nucleotide rebuilt HPV 31 middle L1 fragment. PCR was then used to amplify the wild-type nucleotides 1-725 (5' end) and 1221-1515 (3' end). A final PCR using the 5' end, the 3' end, and the rebuilt middle was performed to generate full-length 31 L1 partial rebuild, referred to herein as the "31 L1 partial rebuild".

The complete 31 L1 sequence was also rebuilt with yeast-preferred codons. This construct is referred to herein as the "31 L1 total rebuild". Nine long overlapping oligomers were used to generate yeast-preferred codon nucleotide sequences from 1-753 and four long overlapping oligomers were used to generate yeast-preferred codon nucleotide sequences from 1207-1515. After amplification and gel purification, these fragments, along with the middle rebuilt section described above (nucleotides 697-1249), were used together in a PCR reaction to generate the full length 31 L1 total rebuild sequence. This piece was generated with BamHI extensions. The gel purified rebuilt 31L1 DNA was digested with BamHI, ligated to BamHI digested pGAL110 expression vector and transformed into *E. coli* DH5 cells. Colonies were screened by PCR for the HPV 31 L1 insert in the correct orientation. Sequence and orientation were confirmed by DNA sequencing.

Plasmid DNA was prepared. *S. cerevisiae* cells were made competent and transformed. The yeast were plated in Leu⁻ sorbitol top-agar on Leu⁻ sorbitol plates and incubated inverted for 3-5 days. Colonies were streaked for isolation on Leu⁻ sorbitol plates. Isolated colonies were subsequently grown in 5 ml of 5×Leu⁻Ade⁻ sorbitol with 1.6% glucose and 4% galactose in rotating tube cultures at 30° C. to induce L1 transcription and protein expression. After 48-72 hours, culture volume equivalent to an OD600=10 was pelleted, supernate removed and the pellets frozen and stored −70° C.

EXAMPLE 3

RNA Preparation

Cell pellets of transformed yeast, which were induced to express HPV 31 L1 by galactose induction, were thawed on ice and suspended in 1 ml of cold DEPC-treated water. Cells were pelleted by centrifugation and the resulting supernatant was removed. The cell pellet was then resuspended in 400 µl TES (10 mM Tris pH7.0, 10 mM EDTA and 0.5% SDS). An equal volume of AE buffer-saturated phenol (50 mM NaOAc and 10 mM EDTA) was added. The tube was vortexed for 10 seconds and heated to 65° C. for 50 minutes with mixing every 10 minutes. The tube was then placed on ice for 5 minutes, followed by centrifugation at 4° C. for 5 minutes. The supernatant was collected and transferred to a sterile tube. An additional 400 µl of phenol was added, the tube vortexed, placed on ice for 5 minutes and centrifuged. The supernatant was transferred to a sterile tube and 400 µl of chloroform added, mixed and centrifuged. The supernatant was again collected and transferred to a sterile tube and 40 µl 3 M Na Acetate pH 5.2 added in addition to 1 ml 100% EtOH. The tube was placed on dry ice for one hour, after which it was centrifuged at high speed to pellet the RNA. The RNA was washed one time with 70% EtOH and air-dried. The RNA was then suspended in 100 µl DEPC-treated water and heated to 65° C. for 5 minutes to dissolve. Spectrophotometry was performed to determine the concentration of RNA in the sample using the assumption that an A260 reading of 1=40 µg/ml RNA when the A260/280 is 1.7-2.0.

EXAMPLE 4

Northern Blot Analysis

Initial analysis of yeast expressing 31 L1 wild-type suggested that the expression yield of HPV 31 L1 protein was considerably less than was expected. To determine if the low expression was occurring due to a problem at the transcription level versus the translation level, Northern blot analysis of the HPV 31 L1 transcript was performed. Northern blots were made from gels in which RNA from yeast expressing HPV16 L1 was run with RNA from yeast expressing HPV31 L1 on the same gel to compare transcript sizes.

A 1.2% agarose formaldehyde gel was cast. Ten micrograms of RNA was combined with denaturing buffer (final concentrations: 6% formaldehyde, 45% formamide and 0.9× MOPS) and heated to 55° C. for 15 minutes. A one-tenth volume of gel loading buffer was added and the sample loaded onto the gel. Electrophoresis was performed at 65 volts in 1×MOPS buffer for ~5 hours. The gel was washed for 15 minutes in sterile water followed by two five minute washes in 10×SSC. The RNA was transferred to a Hybond-N+ nylon membrane (Amersham Biosciences, Piscataway, N.J.) by capillary action over 16 hours in 10×SSC. The RNA was then fixed to the nylon membrane by cross-linking using the Amersham cross-linker set for 700 units of energy. After fixing, the nylon membrane was allowed to air dry. The membrane was placed in 30 ml Zetaprobe buffer at 55° C. for 2 hours after which 32P-labeled probes were added and incubated for 16 hours at 53-65° C. The membrane was then washed 3 times in 5×SSC at room temperature for 20 minutes, followed by 2 times in 0.4×SSC for 20 minutes at room temperature and once at 60° C. for 10 minutes. Probe DNA was generated by PCR using HPV 31 L1 sequence specific sense and antisense primers. The amplified DNA was labeled by treatment with polynucleotide kinase (PNK) and γ-32P ATP at 37° C. for 1 hour. The blot was wrapped in saran wrap and exposed to x-ray film for 16 hours. Upon film development, probe-hybridized RNA was detected as a black band on the autoradiograph.

Analysis of the Northern blot described above revealed that the majority of the full-length HPV 31 L1 wild-type transcripts were considerably smaller than full length (see FIG. 4). However, the 31 L1 partial rebuild was designed not only to insert yeast-preferred codons in the middle of the gene, but also to eliminate any potential sequences resembling yeast transcription termination sites. Northern blot analysis clearly showed that upon rebuilding, the length of the 31 L1 gene transcript had significantly increased to a size corresponding with that of the full-length HPV 16 L1 transcript (not shown). Thus, premature transcription termination is likely to have accounted for a significant portion of the low expression yield from the 31 L1 wild-type construct.

EXAMPLE 5

HPV 31 L1 Protein Expression

Frozen yeast cell pellets of galactose induced cultures equivalent to OD600=10 were thawed on ice and suspended in 300 µl of PC buffer (100 mM $Na_2HPO_4$ and 0.5 M NaCl, pH 7.0) with 2 mM PMSF. Acid-washed 0.5 mm glass beads were added, ~0.5 g/tube. The tubes were vortexed for 15 minutes at 4° C. 7.5 µl of 20% TritonX100 was added and vortex repeated for 5 minutes at 4° C. The tubes were placed on ice for 15 minutes, then centrifuged for 15 minutes at 4° C. The supernate was transferred to a sterile microcentrifuge tube and stored at −70° C.

EXAMPLE 6

Western Blot Analysis

Total yeast protein extract from twenty to forty isolated yeast colonies for each HPV 31 L1 construct were analyzed by Western blot to confirm expression of HPV 31 L1 protein after galactose induction.

Ten micrograms of total yeast protein extract was combined with SDS-PAGE loading buffer and heated to 95° C. for 10 minutes. The proteins were loaded onto an 8% SDS-PAGE gel and electrophoresed in Tris-Glycine buffer. After protein separation, the proteins were Western transferred from the gel to nitrocellulose and the blot was blocked in 10% non-fat dry milk in TTBS (Tris buffered saline with Tween −20) for 16 hours. The blot was washed three times in TTBS. Goat anti-trpE-HPV16 L1 serum, a polyclonal serum that cross-reacts with HPV 31 L1, was applied at a 1:1000 dilution in TTBS for 1 hr at room temperature. The blot was washed three times in TTBS and anti-goat-HRP conjugated antibody was applied at a 1:2500 dilution in TTBS for 1 hr. The blot was again washed three times and ECL™ detection reagent was applied (Amersham Biosciences, Piscataway, N.J.). Autoradiography was then performed. Proteins recognized by the antiserum were visualized by the detection reagent as dark bands on the autoradiograph.

In all cases, the HPV 31 L1 protein was detected as a distinct band on the autoradiograph corresponding to approximately 55 kD (data not shown). The HPV16 L1 protein was included as a positive control on the gels.

EXAMPLE 7

Radioimmunoassay (RIA)

The yeast cells expressing HPV 31 L1 were grown by a variety of methods, including rotating tube cultures, shake flasks and fermenters. The yeast were lysed and protein extracts made to determine the amount of HPV 31 L1 virus-like particles (VLPs) produced per milligram of total protein. To demonstrate HPV 31 L1 VLP expression, a portion of each total yeast protein extract was analyzed by capture radioimmunoassay (RIA).

The RIA was performed using a detection monoclonal antibody, H31.A6, that is HPV type 31-specific and VLP conformational-specific. H31.A6 is specific for HPV type 31 L1 as it is found to bind intact HPV 31 L1 VLPs and does not recognize denatured HPV 31 VLPs. This mAb can be subsequently detected by a goat anti-mouse antibody radiolabeled with 1125. Therefore, the counts per minute (cpm) values correspond to relative levels of HPV31 L1 VLP expression.

Polystyrene beads were coated with a goat anti-trpE-HPV31 L1 polyclonal serum diluted 1:1000 in PBS overnight. The beads were then washed with 5 volumes of sterile distilled water and air-dried. The antigen, total yeast protein extract from isolated yeast colonies, was then loaded onto the beads by dilution in PBS with 1% BSA, 0.1% Tween-20 and 0.1% Na Azide and incubated with rotation for one hour. After washing, the beads were distributed one per well in a 20-well polystyrene plate and incubated with H31.A6 mAb diluted 1:50,000 for 17-24 hours at room temperature. The beads were washed and 1125 labeled goat anti-mouse IgG was added at an activity range of 23000-27000 cpm per 10 µl. After 2 hours, the beads were washed and radioactive counts were recorded in cpm/ml. Background counts from blank wells were subtracted from the total cpm/ml, giving the RIA minus background value.

Two experiments were performed: in experiment 1, protein extracts from 31 L1 wild-type and 31 L1 partial rebuild were compared and in experiment 2, protein extracts from 31 L1 partial rebuild and 31 L1 total rebuild were compared (see FIG. 5). Results indicate that 31 L1 partial rebuild VLP expression is 6.9 fold greater than 31 L1 wild-type. The 31 L1 total rebuild has a 1.7 fold increased expression over the 31 L1 partial rebuild. Therefore, the 31 L1 expression levels were increased >7 fold by introducing yeast-preferred codon sequences and eliminating potential transcription termination signals.

EXAMPLE 8

Transmission Electron Microscopy

Figure 6:
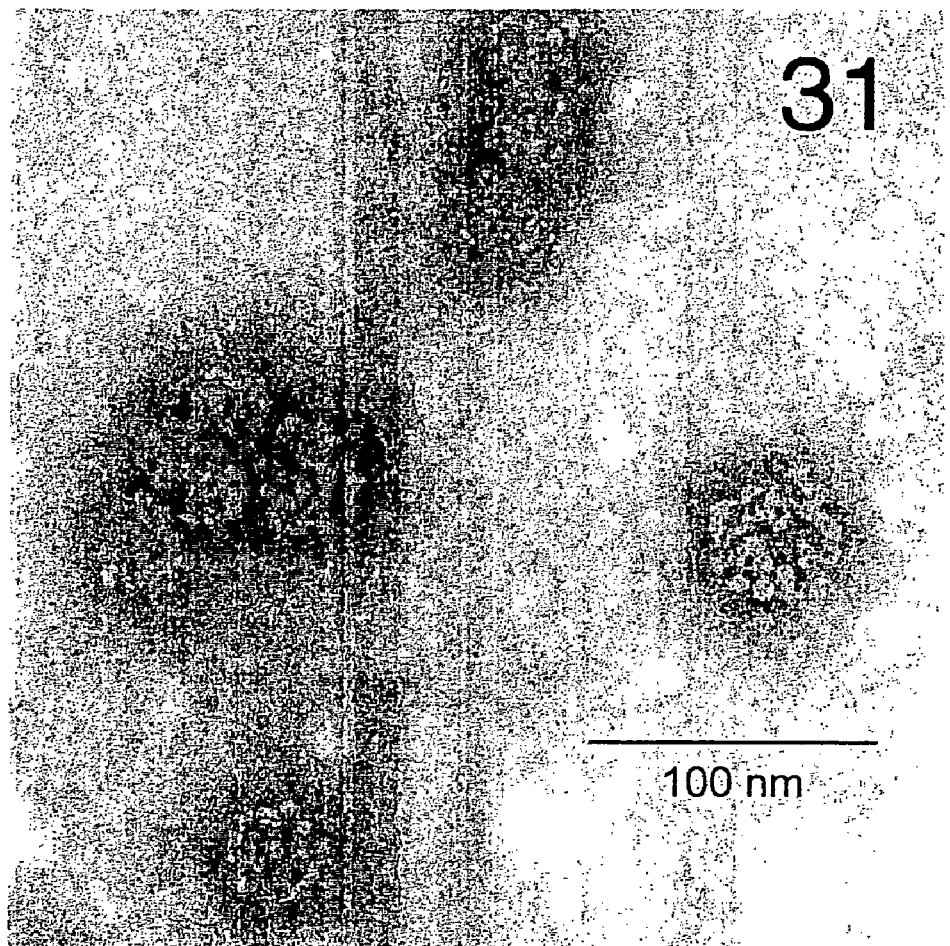
FIG. 6 shows a representative sample of the 31 L1 VLPs described herein, as visualized by transmission electron microscopy (see EXAMPLE 8). The bar represents 100 nm.

To demonstrate that the HPV 31 L1 protein was in fact self-assembling to form pentameric-L1 capsomers, which in turn self-assemble into virus-like particles, a partially purified 31 L1 total rebuild protein extract was subject to transmission electron microscopy (TEM). Yeast were grown under small scale fermentation and pelleted. The pellets were subjected to purification treatments. Pellet and clarified yeast extracts were analyzed by immunoblot to demonstrate L1 protein expression and retention through the purification procedure. Clarified yeast extracts were then subjected to centrifugation over a 45%-sucrose cushion and the resulting pellet suspended in buffer for TEM analysis (see FIG. 6). Results indicated that the diameter of the spherical particles in this crude sample ranged from between 30 and 60 nm with some particles displaying a regular array of capsomers.

The invention claimed is:

1. Virus-like particles (VLPs) comprising recombinant L1 protein or recombinant L1+L2 proteins of HPV31, wherein the recombinant L1 protein or the recombinant L1+L2 proteins are produced in yeast, and wherein the L1 protein is encoded by a codon-optimized HPV31 L1 nucleic acid molecule, which consists essentially of a sequence of nucleotides as set forth in SEQ ID NO:2 or SEQ ID NO:3.

2. A method of producing an HPV31 virus-like particle (VLP), comprising:
   (a) transforming a yeast cell with a nucleic acid molecule encoding an HPV31 L1 protein, the HPV31 L1 protein comprising a sequence of amino acids as set forth in SEQ ID NO:4; wherein the nucleic acid molecule comprises a sequence of nucleotides that is codon-optimized for high level expression in a yeast cell;
   (b) cultivating the transformed yeast cell under conditions that permit expression of the nucleic acid molecule to produce a recombinant papillomavirus protein; and
   (c) isolating the recombinant papillomavirus protein to produce the HPV31 VLP.

3. A vaccine comprising the VLPs of claim 1.

4. Pharmaceutical compositions comprising the VLPs of claim 1.

5. A method of preventing HPV infection comprising administering the vaccine of claim 3 to a mammal.

6. A method for inducing an immune response in an animal comprising administering the VLPs of claim 1 to the animal.

7. The method of claim 2 wherein the yeast is selected from the group consisting of *Saccharomyces cerevisiae, Hansenula polymorpha, Pichia pastoris, Kluyvermyces fragilis, Kluyveromyces lactis,* and *Schizosaceharomyces pombe*.

8. The method of claim 7, wherein the yeast is *Saccharomyces cerevisiae*.

9. The method of claim 2, wherein the nucleic acid molecule comprises a sequence of nucleotides as set forth in SEQ ID NO:2 or SEQ ID NO:3.

10. The method of claim 9, wherein the nucleic acid molecule consists essentially of a sequence of nucleotides as set forth in SEQ ID NO:2 or SEQ ID NO:3.

11. The method of claim 2, wherein step (a) further comprises transforming the yeast cell with a nucleic acid molecule encoding HPV31 L2 protein.

12. A human papillomavirus (HPV) virus-like particle (VLP) comprising recombinant L1 protein of HPV31, wherein the recombinant L1 protein consists essentially of an amino acid sequence as set forth in SEQ ID NO:4.

13. A method for inducing an immune response in an animal comprising administering the HPV31 VLP of claim 12 to the animal.

14. The VLP of claim 12, wherein the VLP is produced in yeast.

* * * * *

SEQUENCE LISTING

<160> NUMBER OF SEQ ID NOS: 8

<210> SEQ ID NO 1
<211> LENGTH: 1515
<212> TYPE: DNA
<213> ORGANISM: HPV31 L1 wild-type

<400> SEQUENCE: 1

```
atgtctctgt ggcggcctag cgaggctact gtctacttac cacctgtccc agtgtctaaa        60
gttgtaagca cggatgaata tgtaacacga accaacatat attatcacgc aggcagtgct       120
aggctgctta cagtaggcca tccatattat tccataccta aatctgacaa tcctaaaaaa       180
atagttgtac caaaggtgtc aggattacaa tatagggtat ttagggttcg tttaccagat       240
ccaaacaaat ttggatttcc tgatacatct ttttataatc ctgaaactca acgcttagtt       300
tgggcctgtg ttggtttaga ggtaggtcgc gggcagccat taggtgtagg tattagtggt       360
catccattat taaataaatt tgatgacact gaaaactcta atagatatgc cggtggtcct       420
ggcactgata atagggaatg tatatcaatg gattataaac aaacacaact gtgtttactt       480
ggttgcaaac cacctattgg agagcattgg ggtaaaggta gtccttgtag taacaatgct       540
```

```
attacccctg gtgattgtcc tccattagaa ttaaaaaatt cagttataca agatggggat      600
atggttgata caggctttgg agctatggat tttactgctt tacaagacac taaaagtaat      660
gttcctttgg acatttgtaa ttctatttgt aaatatccag attatcttaa aatggttgct      720
gagccatatg gcgatacatt atttttttat ttacgtaggg aacaaatgtt tgtaaggcat      780
ttttttaata gatcaggcac ggttggtgaa tcggtcccta ctgacttata tattaaaggc      840
tccggttcaa cagctacttt agctaacagt acatactttc ctacacctag cggctccatg      900
gttacttcag atgcacaaat ttttaataaa ccatattgga tgcaacgtgc tcagggacac      960
aataatggta tttgttgggg caatcagtta tttgttactg tggtagatac cacacgtagt     1020
accaatatgt ctgtttgtgc tgcaattgca aacagtgata ctacatttaa aagtagtaat     1080
tttaaagagt atttaagaca tggtgaggaa tttgatttac aatttatatt tcagttatgc     1140
aaaataacat tatctgcaga cataatgaca tatattcaca gtatgaatcc tgctatttg      1200 gaagattgga atttggatt gaccacacct ccctcaggtt ctttggagga tacctatagg      1260
tttgtaacct cacaggccat tacatgtcaa aaaagtgccc ccaaaagcc caaggaagat      1320 ccatttaaag attatgtatt tgggaggtt aatttaaaag aaaagttttc tgcagattta      1380
gatcagtttc cactgggtcg caaattttta ttacaggcag gatatagggc acgtcctaaa     1440
tttaaagcag gtaaacgtag tgcaccctca gcatctacca ctacaccagc aaaacgtaaa     1500
aaaactaaaa agtaa                                                      1515
```

<210> SEQ ID NO 2
<211> LENGTH: 1515
<212> TYPE: DNA
<213> ORGANISM: Artificial Sequence
<220> FEATURE:
<223> OTHER INFORMATION: 31 partial rebuild

<400> SEQUENCE: 2

```
atgtctctgt ggcggcctag cgaggctact gtctacttac cacctgtccc agtgtctaaa        60
gttgtaagca cggatgaata tgtaacacga accaacatat attatcacgc aggcagtgct       120
aggctgctta cagtaggcca tccatattat tccataccta aatctgacaa tcctaaaaaa       180
atagttgtac caaggtgtc aggattacaa tatagggtat ttagggttcg tttaccagat        240
ccaaacaaat ttggatttcc tgatacatct ttttataatc ctgaaactca acgcttagtt       300
tgggcctgtg ttggtttaga ggtaggtcgc gggcagccat taggtgtagg tattagtggt       360
catccattat taaataaatt tgatgacact gaaaactcta atagatatgc cggtggtcct       420
ggcactgata atagggaatg tatatcaatg gattataaac aaacacaact gtgtttactt       480
ggttgcaaac cacctattgg agagcattgg ggtaaaggta gtccttgtag taacaatgct       540
attacccctg gtgattgtcc tccattagaa ttaaaaaatt cagttataca agatggggat       600
atggttgata caggctttgg agctatggat tttactgctt tacaagacac taaaagtaat       660
gttcctttgg acatttgtaa ttctatttgt aaatatccag attatcttaa aatggttgct       720
gagccatacg gcgacaccct tgttcttcta ttgcgtagag aacagatgtt cgtaaggcac       780
ttcttcaaca gatccggcac cgtaggtgaa tctgtcccaa ccgacctgta catcaagggc       840
tccggttcca ccgctaccct ggctaactcc acctacttcc caactccatc tggctccatg       900
gtcacctccg acgctcagat cttcaacaag ccatactgga tgcagcgtgc acagggtcac       960
aacaacggta tctgttgggg taaccagctg ttcgtgactg tggtcgatac cacgcgttct      1020
accaacatgt ctgtctgtgc tgcaatcgct aactctgaca ctaccttcaa gtcctctaac      1080
```

```
ttcaaggagt acctgagaca tggtgaggaa ttcgatctgc aattcatctt ccagttgtgc    1140
aagatcaccc tgtctgctga catcatgacc tacatccaca gtatgaaccc tgccatcctg    1200
gaggactgga acttcggtct gaccactcca ccttccggtt ctttggagga tacctatagg    1260
tttgtaacct cacaggccat tacatgtcaa aaaagtgccc cccaaaagcc caaggaagat    1320
ccatttaaag attatgtatt tgggaggtt aatttaaaag aaaagttttc tgcagattta    1380
gatcagtttc cactgggtcg caaatttta ttacaggcag gatataggc acgtcctaaa    1440 tttaaagcag gtaaacgtag tgcaccctca gcatctacca ctacaccagc aaaacgtaaa    1500
aaaactaaaa agtaa                                                    1515

<210> SEQ ID NO 3
<211> LENGTH: 1515
<212> TYPE: DNA
<213> ORGANISM: Artificial Sequence
<220> FEATURE:
<223> OTHER INFORMATION: 31 total rebuild

<400> SEQUENCE: 3
atgtctttgt ggagaccatc tgaagctacc gtctacttgc caccagtccc agtctctaag      60
gtcgtctcta ccgacgaata cgtcaccaga accaacatct actaccacgc tggttctgct    120
agattgttga ccgtcggtca cccatactac tctatcccaa agtctgacaa cccaaagaag    180
atcgtcgtcc caaggtctc tggttttgcaa tacagagtct tcagagtcag attgccagac    240
ccaaacaagt tcggtttccc agacacctct ttctacaacc cagaaaccca agattggtc    300 tgggcttgtg tcggtttgga agtcggtaga ggtcaaccat gggtgtcgg tatctctggt    360 cacccattgt tgaacaagtt cgacgacacc gaaaactcta cagatacgc tggtggtcca    420 ggtaccgaca cagagaatg tatctctatg gactacaagc aaacccaatt gtgtttgttg    480
ggttgtaagc caccaatcgg tgaacactgg ggtaaggttt ctccatgttc taacaacgct    540 atcacccag gtgactgtcc accattggaa ttgaagaact ctgtcatcca agacggtgac    600
atggtcgaca ccggtttcgg tgctatcgac ttcaccgctt tgcaagacac caagtctaac    660
gtcccattgg acatctgtaa ctctatctgt aagtacccag actacttgaa gatggtcgct    720
gaaccatacg cgacaccctt gttcttctac ttgcgtagag aacagatgtt cgtaaggcac    780
ttcttcaaca gatccggcac cgtaggtgaa tctgtcccaa ccgacctgta catcaagggc    840
tccggttcca ccgctacccct ggctaactcc acctacttcc caactccatc tggctccatg    900
gtcacctccg acgctcagat cttcaacaag ccatactgga tgcagcgtgc acagggtcac    960
aacaacggta tctgttgggg taaccagctg ttcgtgactg tggtcgatac cacgcgttct   1020
accaacatgt ctgtctgtgc tgcaatcgct aactctgaca ctaccttcaa gtcctctaac   1080
ttcaaggagt acctgagaca tggtgaggaa ttcgatctgc aattcatctt ccagttgtgc   1140
aagatcaccc tgtctgctga catcatgacc tacatccaca gtatgaaccc tgccatcctg   1200
gaggactgga acttcggtct gaccactcca ccttccggtt ctttggaaga cacctacaga   1260
ttcgtcacct ctcaagctat cacctgtcaa aagtctgctc cacaaaagcc aaaggaagac   1320
ccattcaagg actacgtctt ctgggaagtc aacttgaagg aaaagttctc tgctgacttg   1380
gaccaattcc cattgggtag aaagttcttg ttgcaagctg gttacagagc tagaccaaag   1440
ttcaaggctg gtaagagatc tgctccatct gcttctacca ccaccccagc taagagaaag   1500
aagaccaaga agtaa                                                   1515
```

<210> SEQ ID NO 4
<211> LENGTH: 504
<212> TYPE: PRT
<213> ORGANISM: Artificial Sequence
<220> FEATURE:
<223> OTHER INFORMATION: HPV 31 L1

<400> SEQUENCE: 4

```
Met Ser Leu Trp Arg Pro Ser Glu Ala Thr Val Tyr Leu Pro Pro Val
 1               5                  10                  15

Pro Val Ser Lys Val Val Ser Thr Asp Glu Tyr Val Thr Arg Thr Asn
            20                  25                  30

Ile Tyr Tyr His Ala Gly Ser Ala Arg Leu Leu Thr Val Gly His Pro
        35                  40                  45

Tyr Tyr Ser Ile Pro Lys Ser Asp Asn Pro Lys Lys Ile Val Val Pro
    50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Glu Thr
                85                  90                  95

Gln Arg Leu Val Trp Ala Cys Val Gly Leu Glu Val Gly Arg Gly Gln
            100                 105                 110

Pro Leu Gly Val Gly Ile Ser Gly His Pro Leu Leu Asn Lys Phe Asp
        115                 120                 125

Asp Thr Glu Asn Ser Asn Arg Tyr Ala Gly Gly Pro Gly Thr Asp Asn
    130                 135                 140

Arg Glu Cys Ile Ser Met Asp Tyr Lys Gln Thr Gln Leu Cys Leu Leu
145                 150                 155                 160

Gly Cys Lys Pro Pro Ile Gly Glu His Trp Gly Lys Gly Ser Pro Cys
                165                 170                 175

Ser Asn Asn Ala Ile Thr Pro Gly Asp Cys Pro Pro Leu Glu Leu Lys
            180                 185                 190

Asn Ser Val Ile Gln Asp Gly Asp Met Val Asp Thr Gly Phe Gly Ala
        195                 200                 205

Met Asp Phe Thr Ala Leu Gln Asp Thr Lys Ser Asn Val Pro Leu Asp
    210                 215                 220

Ile Cys Asn Ser Ile Cys Lys Tyr Pro Asp Tyr Leu Lys Met Val Ala
225                 230                 235                 240

Glu Pro Tyr Gly Asp Thr Leu Phe Phe Tyr Leu Arg Arg Glu Gln Met
                245                 250                 255

Phe Val Arg His Phe Phe Asn Arg Ser Gly Thr Val Gly Glu Ser Val
            260                 265                 270

Pro Thr Asp Leu Tyr Ile Lys Gly Ser Gly Thr Ala Thr Leu Ala
        275                 280                 285

Asn Ser Thr Tyr Phe Pro Thr Pro Ser Gly Ser Met Val Thr Ser Asp
    290                 295                 300

Ala Gln Ile Phe Asn Lys Pro Tyr Trp Met Gln Arg Ala Gln Gly His
305                 310                 315                 320

Asn Asn Gly Ile Cys Trp Gly Asn Gln Leu Phe Val Thr Val Val Asp
                325                 330                 335

Thr Thr Arg Ser Thr Asn Met Ser Val Cys Ala Ala Ile Ala Asn Ser
            340                 345                 350

Asp Thr Thr Phe Lys Ser Ser Asn Phe Lys Glu Tyr Leu Arg His Gly
        355                 360                 365
```

```
Glu Glu Phe Asp Leu Gln Phe Ile Phe Gln Leu Cys Lys Ile Thr Leu
    370                 375                 380

Ser Ala Asp Ile Met Thr Tyr Ile His Ser Met Asn Pro Ala Ile Leu
385                 390                 395                 400

Glu Asp Trp Asn Phe Gly Leu Thr Thr Pro Pro Ser Gly Ser Leu Glu
                405                 410                 415

Asp Thr Tyr Arg Phe Val Thr Ser Gln Ala Ile Thr Cys Gln Lys Ser
                420                 425                 430

Ala Pro Gln Lys Pro Lys Glu Asp Pro Phe Lys Asp Tyr Val Phe Trp
            435                 440                 445

Glu Val Asn Leu Lys Glu Lys Phe Ser Ala Asp Leu Asp Gln Phe Pro
    450                 455                 460

Leu Gly Arg Lys Phe Leu Leu Gln Ala Gly Tyr Arg Ala Arg Pro Lys
465                 470                 475                 480

Phe Lys Ala Gly Lys Arg Ser Ala Pro Ser Ala Ser Thr Thr Thr Pro
                485                 490                 495

Ala Lys Arg Lys Lys Thr Lys Lys
            500

<210> SEQ ID NO 5
<211> LENGTH: 34
<212> TYPE: DNA
<213> ORGANISM: Artificial Sequence
<220> FEATURE:
<223> OTHER INFORMATION: PCR Primer

<400> SEQUENCE: 5
cgtcgacgta aacgtgtatc atatttttt acag                    34

<210> SEQ ID NO 6
<211> LENGTH: 25
<212> TYPE: DNA
<213> ORGANISM: Artificial Sequence
<220> FEATURE:
<223> OTHER INFORMATION: PCR Primer

<400> SEQUENCE: 6
cagacacatg tattacatac acaac                             25

<210> SEQ ID NO 7
<211> LENGTH: 41
<212> TYPE: DNA
<213> ORGANISM: Artificial Sequence
<220> FEATURE:
<223> OTHER INFORMATION: PCR Primer

<400> SEQUENCE: 7
ctcagatctc acaaaacaaa atgtctctgt ggcggcctag c            41

<210> SEQ ID NO 8
<211> LENGTH: 38
<212> TYPE: DNA
<213> ORGANISM: Artificial Sequence
<220> FEATURE:
<223> OTHER INFORMATION: PCR Primer

<400> SEQUENCE: 8
gacagatctt acttttagt tttttacgt tttgctgg                  38
```